(12) United States Patent
Machiya et al.

(10) Patent No.: US 7,326,176 B2
(45) Date of Patent: Feb. 5, 2008

(54) ENDOSCOPE ANGLE PORTION

(75) Inventors: Mamoru Machiya, Saitama (JP); Haruo Akiba, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 233 days.

(21) Appl. No.: 11/135,294

(22) Filed: May 24, 2005

(65) Prior Publication Data
US 2005/0261548 A1 Nov. 24, 2005

(30) Foreign Application Priority Data
May 24, 2004 (JP) ............................. 2004-153493

(51) Int. Cl.
*A61B 1/00* (2006.01)
(52) U.S. Cl. ...................... 600/142; 600/141; 600/129; 600/146; 600/149
(58) Field of Classification Search ................ 600/139, 600/141, 142, 146
See application file for complete search history.

(56) References Cited

U.S. PATENT DOCUMENTS

| 4,351,323 | A |   | 9/1982 | Ouchi et al. |   |
|---|---|---|---|---|---|
| 4,530,568 | A | * | 7/1985 | Haduch et al. | 385/118 |
| 5,174,277 | A | * | 12/1992 | Matsumaru | 600/142 |
| 5,178,129 | A | * | 1/1993 | Chikama et al. | 600/142 |
| 5,179,935 | A |   | 1/1993 | Miyagi |   |
| 6,402,686 | B1 | * | 6/2002 | Ouchi | 600/139 |
| 6,837,849 | B2 | * | 1/2005 | Ogura et al. | 600/146 |
| 2002/0032371 | A1 |   | 3/2002 | Torri |   |
| 2003/0045778 | A1 | * | 3/2003 | Ohline et al. | 600/114 |
| 2004/0044270 | A1 | * | 3/2004 | Barry | 600/142 |

FOREIGN PATENT DOCUMENTS

| EP | 1 090 581 A1 | 4/2001 |
|---|---|---|
| EP | 1 366 705 A1 | 12/2003 |
| JP | 3-218723 | 9/1991 |

* cited by examiner

*Primary Examiner*—John P. Leubecker
*Assistant Examiner*—Victoria W. Chen
(74) *Attorney, Agent, or Firm*—Oblon, Spivak, McClelland, Maier & Neustadt, P.C.

(57) ABSTRACT

An endoscope angle portion comprises an angle portion structure. The angle portion structure includes angle ring units each of which comprises pivoting joint portions extending from its both ends and has a shape that is notched obliquely in directions away from the pivoting joint portions, and wherein adjacent ones of the angle ring units is pivotally joined to form the angle portion structure, wherein a first angle ring unit of the angle ring units has a larger length dimension than that of a second angle ring unit of the angle ring units, and the first angle ring unit has a smaller notch width of a notched portion than that of the second angle ring unit, the first angle ring unit being nearer a base end of the endoscope angle portion than the second angle ring unit.

2 Claims, 5 Drawing Sheets

ENDOSCOPE ANGLE PORTION

BACKGROUND OF THE INVENTION

1. Field of the Invention

This invention relates to the structure of an angle portion that makes up an insertion portion of an endoscope used for medical use, etc.

2. Description of the Related Art

Generally, with an endoscope for medical use, etc., an insertion portion, for insertion into a body cavity, etc., is connected to a body control portion, and a universal cable, which is detachably connected at least to a light source device, is lead out to the body control portion. The insertion portion comprises, in the order from the side connected to the body control portion, a flexible portion, an angle portion, and a distal end hard portion, and the angle portion, which is connected to the front end of the flexible portion, which can be bent in an arbitrary direction in accordance with an insertion path of the insertion portion, is a portion that can be operated to become bent by an angle control section disposed at the body control portion. An endoscopic observation mechanism, comprising an illumination portion and an observation portion, is mounted to the distal end hard portion, and by performing a bending operation of the angle portion, the direction of the distal end hard portion can be controlled to thereby orient the distal end hard portion towards an insertion path or change the endoscopic observation field.

In regard to the structure of the angle portion, an angle portion structure, equipped with a predetermined number of angle rings, is formed by pivotally joining the angle rings to each other in the front/rear direction successively by means of pivoting joint pins. The outer periphery of the angle portion structure is covered with a net, and this net is furthermore covered with an outer sheath layer formed of a flexible member. The interior of the angle portion structure is thus a passage of a cylindrical shape, and various members are inserted into this passage. Members inserted into this passage include a light guide that transmits illumination light and a signal cable that extends from a solid-state image pickup element disposed at the observation portion (an image guide in the case of an optical endoscope), and an operative instrument insertion channel, an air/water feed tube, etc., are also inserted into this passage.

Here, at the rigid front end part, the front end of the operative instrument insertion channel opens to a position near the observation portion. When an affected part, etc., is found while observing the interior of a body cavity by the endoscopic observation mechanism, the operative instrument insertion channel is used to perform a curative procedure, sampling of tissue, or injection of a medical solution, etc., and a forceps or other operative instrument is inserted into the channel with the insertion portion being inserted inside the body cavity. The operative instrument insertion channel extends into the insertion portion from the body control portion and the portions from the body control portion to the portion connected to the distal end hard portion are formed of a flexible tube that can be bent in arbitrary directions.

In order to enable bending of the angle portion, the angle rings in the front/rear direction are connected in a mutually inclinable manner, and pivoting joint portions are pivotally joined at two locations along the circumference of each angle ring that are separated by 180°. With each angle ring, notched portions are formed obliquely in directions of 90° from each pivoting joint portion, and the angle of inclination of angle rings in the front/rear direction is controlled by the angle of the notched portions. The curvature of bending of the angle portion is thus determined by the length dimension of each angle ring and the inclination angle, that is, the notch width of each notched portion. When the angle rings are pivotally joined at the left and right sides, the angle portion can bend as a whole in the upward and downward directions and when pivotal joining at the left and right sides and at the front and rear are repeated in that order, the angle portion can bend as a whole in the four directions of leftward, rightward, upward, and downward.

In order to make the angle portion become bent by remote operation, two to four angle operating wires are extended from a take-up reel that makes up an angle operating device provided in the body control portion, and these angle operating wires are extended in a manner enabling pushing and pulling operations while being positioned in the circumferential direction by wire guides inside the angle portion. When, for example, the angle portion is to be bent in the upward or downward direction, one of the pair of angle operating wires that are positioned at upper and lower positions is pulled and the other is operated so as to be drawn out. The angle portion is provided for performing the operation of directing the distal end hard portion to a desired direction, and in order to enable the change of direction of the endoscopic observation field at the distal end hard portion from the frontward to the rearward direction, the angle of curvature in at least one direction should be no less than 180° and preferably no less than 200°. The length of the angle portion and the shapes of the angle rings, which form the structural body of the angle portion, are set with the maximum angle of curvature as a basis.

The angle portion is operated to become bent inside a narrow body cavity and thus the locus of the movement of the angle portion in a bending operation is preferably made as compact as possible. Meanwhile, since an operative instrument may be inserted into the operative instrument insertion channel even with the angle portion being bent, the radius of curvature in the maximum bent state is preferably as large as possible in order to enable smooth insertion of the operative instrument.

Here, an arrangement, wherein the length dimensions of the angle rings and the positions of the wire guides, provided for positioning the angle operating wires in the circumferential direction, are varied in the axial line direction to control the bending shape of the angle portion, is disclosed, for example, in JP-A-3-218723.

With the above-mentioned related-art, by making the angle rings decrease continuously in length towards the front end side of the angle portion, that is, towards the side of connection to the distal end hard portion, the radius of curvature of bending of the angle portion is made small, and as a result of the angle portion thus being made compact in movement and the locus of movement of the rigid front end part, in the process of performing a bending operation of the angle portion inside a narrow body cavity, being made compact, the rigid front end part is prevented from becoming pressed strongly against the inner walls of the body cavity during this operation, thereby alleviating the pain that is inflicted on a subject and improving the operability of the angle portion.

However, it is required that the ease of insertion of an operative instrument into the operative instrument insertion channel be good even when the angle portion is in a bent state. Though the operative instrument that is inserted into the operative instrument insertion channel may be a flexible member, such as a tube, the operative instrument may instead be a forceps or other considerably rigid object, which has forceps claws and a forceps claw opening/closing mechanism disposed at the front end and thus with which a portion of some length in the axial line direction is a rigid portion. When the angle portion is bent, the operative instrument insertion channel, which is inserted in the interior thereof also becomes bent at substantially the same curvature as the angle portion, and in the maximally bent state, the operative instrument insertion channel will also become bent sharply. Insertion of a forceps or other operative instrument of poor insertion condition in a passage that is sharply bent in this manner accompanies high resistance against insertion and not only is the operability poor but the inner surface of the operative instrument insertion channel may become pressed by the front end portion of the operative instrument and the flexible tube that makes up the operative instrument insertion channel may become deformed or damaged, etc.

SUMMARY OF THE INVENTION

This invention has been made in view of the above points, and an object thereof is to provide an angle portion that can be bent to the required angle of curvature while making the locus of movement of the angle portion during a bending operation as compact as possible and yet making the radius of curvature during bending as large as possible.

In order to achieve the above object, the present invention provides in an endoscope angle portion, having an angle portion structure, comprising a predetermined number of angle ring units, each angle ring unit having pivoting joint portions extending from both ends thereof and having a shape that is notched obliquely in directions away from the pivoting joint portions, and wherein the angle portion structure is formed by pivotally joining the angle ring units in the front/rear direction, an endoscope angle portion characterized in that with angle ring units at a base end side and angle ring units at a front end side among the angle ring units forming the angle portion structure, the angle ring units at the base end side are made larger in length dimension and smaller in notch width of the notched portion.

In other words, according to the invention, there is provided an endoscope angle portion comprising an angle portion structure including angle ring units each of which comprises pivoting joint portions extending from its both ends and has a shape that is notched obliquely in directions away from the pivoting joint portions, and wherein adjacent ones of the angle ring units is pivotally joined to form the angle portion structure, wherein a first angle ring unit of the angle ring units has a larger length dimension than that of a second angle ring unit of the angle ring units, and the first angle ring unit has a smaller notch width of a notched portion than that of the second angle ring unit, the first angle ring unit being nearer a base end of the endoscope angle portion than the second angle ring unit.

Each angle ring is arranged from a member of cylindrical shape that has extending portions formed at the left and right sides or pairs of extending portions formed at the left/right sides and upper/lower sides, respectively, as pivoting joint portions, and angle rings in the front/rear direction are connected by joining and stopping the pivoting joint portions by means of pivoting joint pins. When respective pairs of the pivoting joint portions at the left/right sides are pivotally joined to each other, the angle portion can be bent in upward and downward directions. When the pivoting joint portions at the upper/lower sides and left/right sides are joined in an alternating manner, the angle portion can be bent in the four directions of upward, downward, leftward, and rightward. In the case where such bending in four directions is enabled, each pair of angle rings that are pivotally joined at the upper/lower sides function as a single, integral unit during bending in the upward and downward directions. In the case of an arrangement enabling bending in two directions, each angle ring unit is a single angle ring, and in the case of an arrangement enabling bending in four directions, each angle ring unit is a set of two angle rings.

Generally, in the case of an arrangement enabling bending in four directions, the maximum curvature of bending is enabled for bending in the upward direction. As the angle ring unit in this case, a pair of front and rear angle rings, which are pivotally joined so as to enable bending in the left and right directions, make up a single angle ring unit. In other words, each of the angle ring units comprises a pair of angle rings so as to bend to a left direction and right direction of the endoscope angle portion, and the angle ring units are provided in an axial line direction of the endoscope angle portion so that the angle portion structure can bend upward and downward.

The length dimension of an angle ring unit is the interval between two pivoting joint portions, positioned at one side and the other side, respectively, and extending in the same direction in the circumferential direction. To be more precise, the length dimension is the interval between the central positions of pivoting joint pins that are fixed to the pivoting joint portions. Portions of each angle ring in the direction of approximately 90° from each pivoting joint portion are inclined obliquely and these inclined portions are the notched portions, and the width dimension of each notched portion is determined by the angle of inclination at the notched portion. The length dimension and the notch width of each angle ring unit are set as described above, and in the axial line direction of the angle portion, the shapes of the angle ring units are varied in a continuous manner or in a step-like manner. In the case of continuous variation, a plurality of types of angle rings that differ in dimensions are used. With an arrangement in which the shapes are varied in a step-like manner, the number of types of angle rings used can be made low. It is thus preferable to vary the angle ring units in a step-like manner and most preferably, the angle ring units are varied in approximately two or three steps. In this case, by making the length dimension of each angle ring unit and the notch width dimension of each notched portion change at the front and rear of a boundary, corresponding to positions of an arc spanning approximately ¼th of a circle formed at the base end side when the angle portion structure is bent to the maximum curvature of bending, the locus of movement of the distal end hard portion during bending operation of the angle portion can be made as compact as possible and yet the radius of curvature during bending can be made large. In other words, third angle ring units of the angle ring units form an arc spanning approximately ¼th of a circle in the state in which the angle portion structure is bent to the maximum curvature of bending, the third angle ring units being nearest the base end of the endoscope angle portion, and an angle ring unit adjacent to the distal one of the third angle ring units has a different length dimension from that of the distal one of the third angle ring units, and has a different notch width of a notched portion from that of the distal one of the third angle ring units.

DETAILED DESCRIPTION OF THE INVENTION

Figure 1:
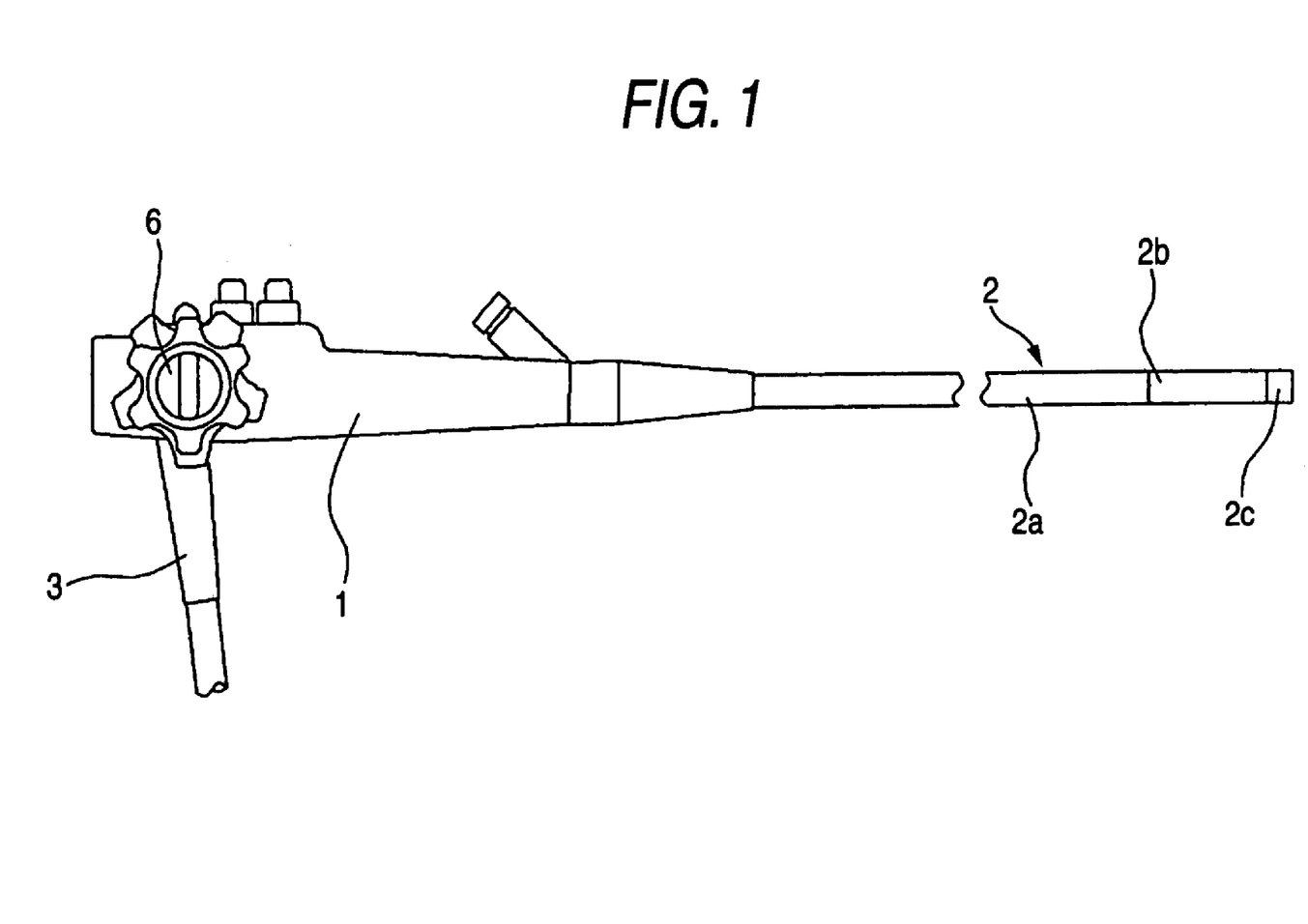
FIG. 1 is an overall arrangement diagram of an endoscope equipped with an angle portion of the present invention.

An embodiment of the present invention shall now be described with reference to the drawings. FIG. 1 shows the overall arrangement of an endoscope and FIG. 2 shows a cross section of a front end section of an insertion portion.

Firstly, in FIG. 1, 1 is a body control portion, 2 is an insertion portion, and 3 is a universal cable. The body control portion 1 is held by one hand and operated by an operating surgeon or other endoscope operator, and the insertion portion 2 is inserted inside a body cavity. The universal cable 3 is equipped with a light source connector, the other end of which is detachably connected to a light source device. A connector for connection to a processor, which is provided integral to or separate from the light source device, is also equipped in the case of an electronic endoscope. The arrangement of the end section of the universal cable 3 is well known and illustration and description thereof shall be omitted.

The insertion portion 2 has a section of predetermined length from the portion connected to the body control portion 1 arranged as a flexible portion 2a, which can be bent in an arbitrary direction in accordance with the insertion path of the insertion portion. An angle portion 2b is connected to the front end of the flexible portion 2a, and a distal end hard portion 2c is connected to the front end of the angle portion 2b. As shown in FIG. 2, an endoscopic observation mechanism 4, comprising an illumination portion and an observation portion, is provided on the front end face (or front end side face) of the distal end hard portion 2c, and an operative instrument insertion channel 5 opens at a position near the observation portion. The angle portion 2b is for controlling the direction of insertion of the distal end hard portion 2c and changing the endoscopic observation field of the endoscopic observation mechanism 4. In order to provide a wide view field from the front to the rear of the inserted instrument 2 as the endoscopic observation field, the angle portion 2b can be bent to an angle of curvature of no less than 180° and preferably no less than 200°.

Figure 2:
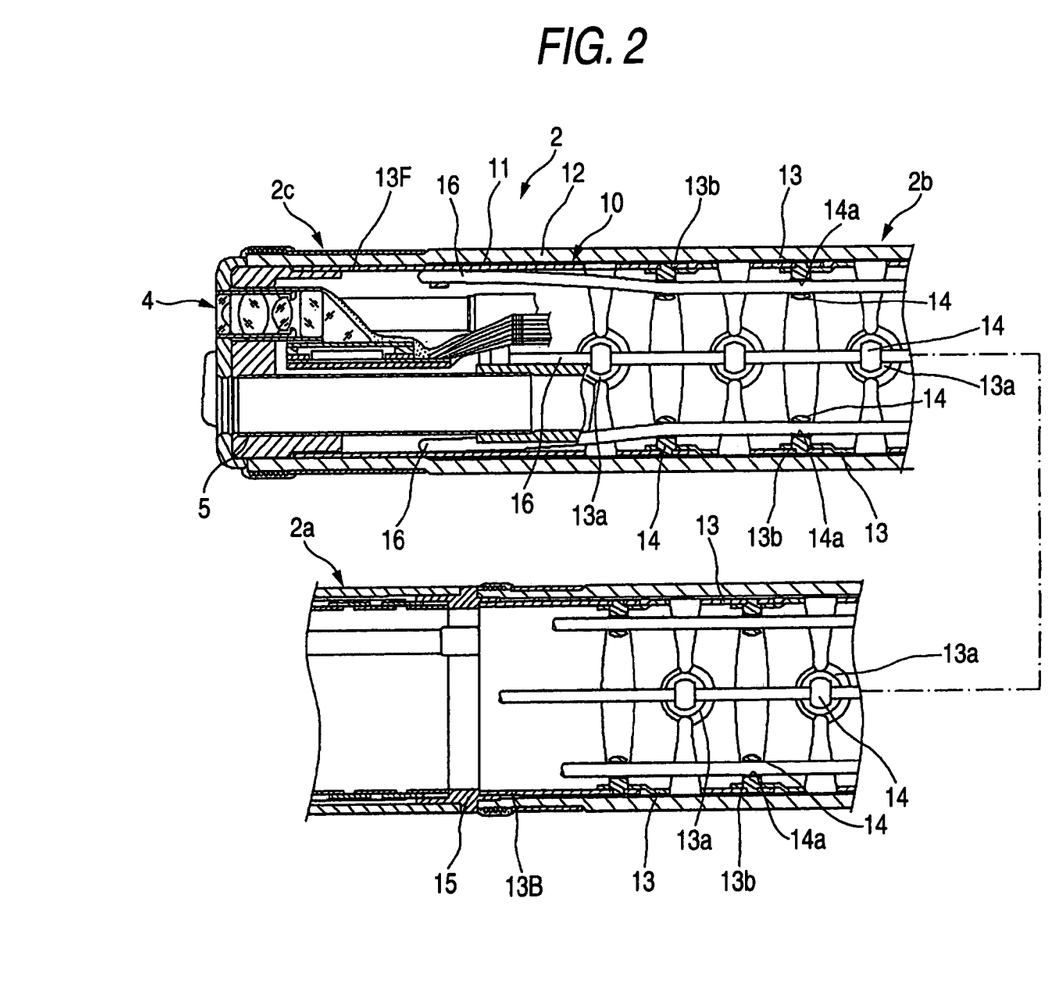
FIG. 2 is a sectional view of the angle portion of FIG. 1.

The arrangement of the angle portion 2b is shown in FIG. 2. The angle portion 2b has an angle portion structure 10, the interior of which forms a circular passage, and this angle portion structure 10 is covered by a net 11. The net 11 is furthermore covered by an outer sheath 12, formed of an elastic member. The angle portion structure 10 is thus the structural body of the angle portion 2b, and although omitted from illustration, the various members indicated in the description of the related-art are inserted into its internal passage. The angle portion structure 10 has a high strength in the direction of compression, and angle rings 13 are thus formed of metal.

The angle portion structure 10 is formed by pivotally joining the angle rings 13 successively, and at the respective ends thereof are disposed a base end connection ring 13B, which is connected to the flexible portion 2a, and a front end connection ring 13F, which is connected to the distal end hard portion 2c. Each angle ring 13 is an annular member having pivoting joint portions 13a and 13b provided at the respective sides, and these pivoting joint portions 13a and 13b are formed as flat portions. The pivoting joint portions 13a at one end side are provided as a pair in a positional relationship of 180° with respect to each other, and the pivoting joint portions 13b at the other end side are provided as a pair in a positional relationship of 90° with respect to the pivoting joint portions 13a at the one end side. These pivoting joint portions 13a and 13b, respectively, have pin insertion holes formed therein, and by joining the respective pivoting joint portions 13a or joining the respective pivoting joint portions 13b of angle rings 13 in the front/rear direction and stopping by means of pivoting joint pins 14, the angle rings 13 in the front/rear direction are joined in a manner enabling rotation relative to each other about the axes of pivoting joint pins 14. For example, at a portion at which the left and right pivoting joint portions 13a of angle rings 13 in the front/rear direction are pivotally joined to each other, the angle rings 13 in the front/rear direction are rotatable in the upward and downward directions. Meanwhile, a portion, at which the upper and lower pivoting joint portions 13b are pivotally joined to each other, is enabled to rotate in the leftward and rightward directions.

Among the base end and front end connection rings 13B and 13F at the respective ends of the angle portion structure 10, the base end connection ring 13B has pivoting joint portions for connection to an angle ring 13 positioned at the front thereof, is not provided with pivoting joint portions at the base end side, and is connected and fixed by soldering or other means to a connection ring 15 to the flexible portion 2. The front end connection ring 13F is equipped with pivoting joint portions for connection to an angle ring 13 to the rear thereof but is not provided with pivoting joint portions at the front end side thereof. This front end connection ring 13F is fitted into and fixed by a set screw or other means to a base end portion of the distal end hard portion 2c.

The angle portion 2b is arranged so that it can be bent by remote operation by an angle operating device 6, disposed at the body control portion 1. A wire guide hole 14a is thus bored in each pivoting joint pin 14, operating wires 16 are inserted through these wire guide holes 14a, and the front end portion of each operating wire 16 is fixed to the front end connection ring 13F. The guides for operating wires 16 may instead be arranged from cut-and-constricted portions provided on the angle rings 13.

Figure 3:
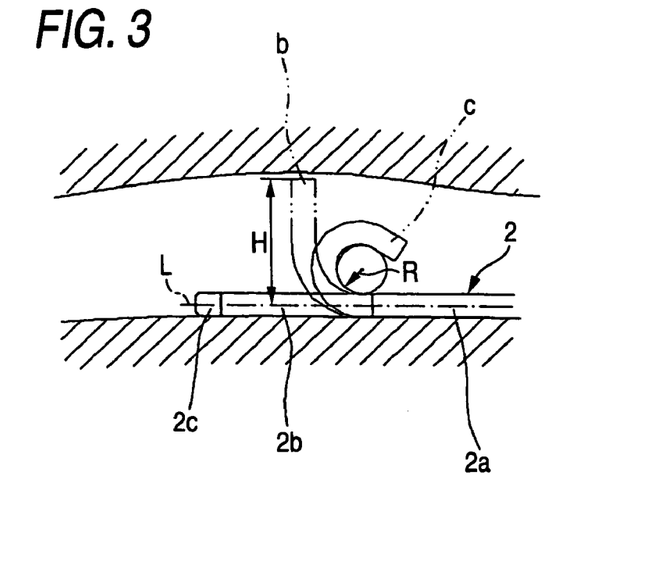
FIG. 3 is an action explanation diagram of the action states of an insertion portion.

FIG. 3 shows a state in which the insertion portion 2 of the endoscope with the above-described arrangement is inserted inside a body cavity. Inside this body cavity, the distal end hard portion 2c can be changed in direction to thereby the direction of the endoscopic observation field from the front side of the insertion portion 2 to the rear side. For this purpose, the angle portion 2b is operated to bend, and in this process of bending the angle portion 2b, the orientation state, which is attained when the angle portion 2b is bent, from the state of being directed straightly forward as indicated by the solid lines, to a right angle with respect to the straight state, is indicated as b in the figure, and the orientation state, at which the maximum angle of curvature is attained, is indicated as c in the figure.

The upright height H of the angle portion 2b in the orientation state b must be made low. When this height H becomes high, the distal end hard portion 2c becomes pressed against the inner wall of the body cavity in the process of changing direction. As a result, the resistance during the bending operation becomes large and severe pain is inflicted on the subject as well. Furthermore, if the height H becomes significantly high, the inner walls of the body cavity may become damaged. The operative instrument insertion channel 5 is inserted through the interior of the angle portion 2b, and since this operative instrument insertion channel 5 becomes bent at substantially the same curvature as the curvature of bending of the angle portion 2b, if the radius of curvature of the angle portion 2b is small, the operative instrument insertion channel 5 will become bent sharply accordingly. The operation of inserting an operative instrument inside the operative instrument insertion channel 5 is thus made difficult. In particular, in the case of a forceps, etc., that has a hard portion of predetermined length at the front end portion, the resistance against insertion inside the operative instrument insertion channel 5 becomes extremely large and in extreme cases, the operative instrument may become locked in the middle. Furthermore, in order to realize a large variation of the endoscopic observation field, the angle portion 2b is enabled to become bent by no less than 180° in at least one direction in the maximally bent state.

When with an arrangement wherein the angle portion 2b is enabled to become bent in the four directions of upward, downward, leftward, and rightward, the same angle of curvature is not enabled for all of these directions but arrangements are made so that the angle of curvature will be maximized for one of the directions, specifically, the upward direction, and when the observation field of the endoscopic observation mechanism is to be directed towards the rear, the angle portion 2b is generally bent upwards, that is, in the direction shown in FIG. 3. Arrangements are thus made so that in the state in which the angle portion 2b is erected to an angle of 90° from the axial line of the insertion portion in the upwardly bending operation, the upright height dimension H from the axial central line L of the insertion portion will be restrained to the minimum and yet the radius of curvature R at the state of the maximum angle of curvature is made as large as possible.

When in the case where the angle portion 2b is enabled to be bent in the four directions of upward, downward, leftward, and rightward, the angle portion 2b is bent upward, each set of two angle rings 13, among the angle rings 13 in the front/rear direction, with which the pivoting joint parts 13b are pivotally joined, become practically integrated in the process of bending in the upward/downward direction. Such an angle ring unit is indicated by the symbol 13U in FIG. 4. Though in the case of an arrangement wherein bending in the two directions of upward and downward is enabled, each angle ring unit 13U is arranged from a single angle ring, in the case of an arrangement enabling bending in the four directions of upward, downward, leftward, and rightward, each angle ring unit 13U is arranged from two angle rings 13 in the front/rear directions.

Figure 4:
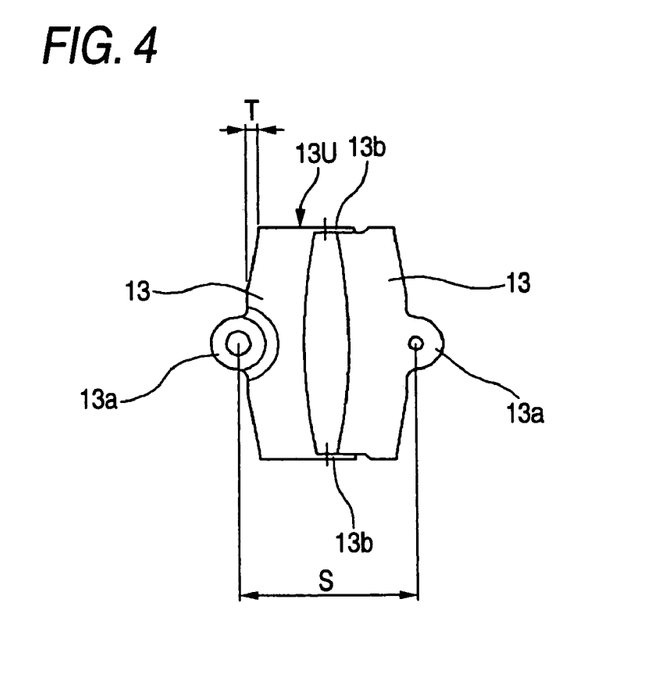
FIG. 4 is a front view of an angle ring unit.

Here, where S is the length dimension of the angle ring unit 13U in the axial line direction. This length dimension S is the interval from the center of the pivoting joint pin 14, mounted to one of the pivoting joint portions 13a, and the center of the pivoting joint pin 14, mounted to the other pivoting joint portion 13a. Also, where the interval in the axial line direction of the notched portion of the angle ring unit 13U is the notch width T. Each angle ring unit 13U is then arranged as described below in order to restrain the height dimension H, when the angle portion 2b is directed upward and bent to a state of an angle of 90° with respect to the axial line of the insertion portion 2, to the minimum and yet make large the radius of curvature R when the maximum angle of curvature is attained.

Figure 5:
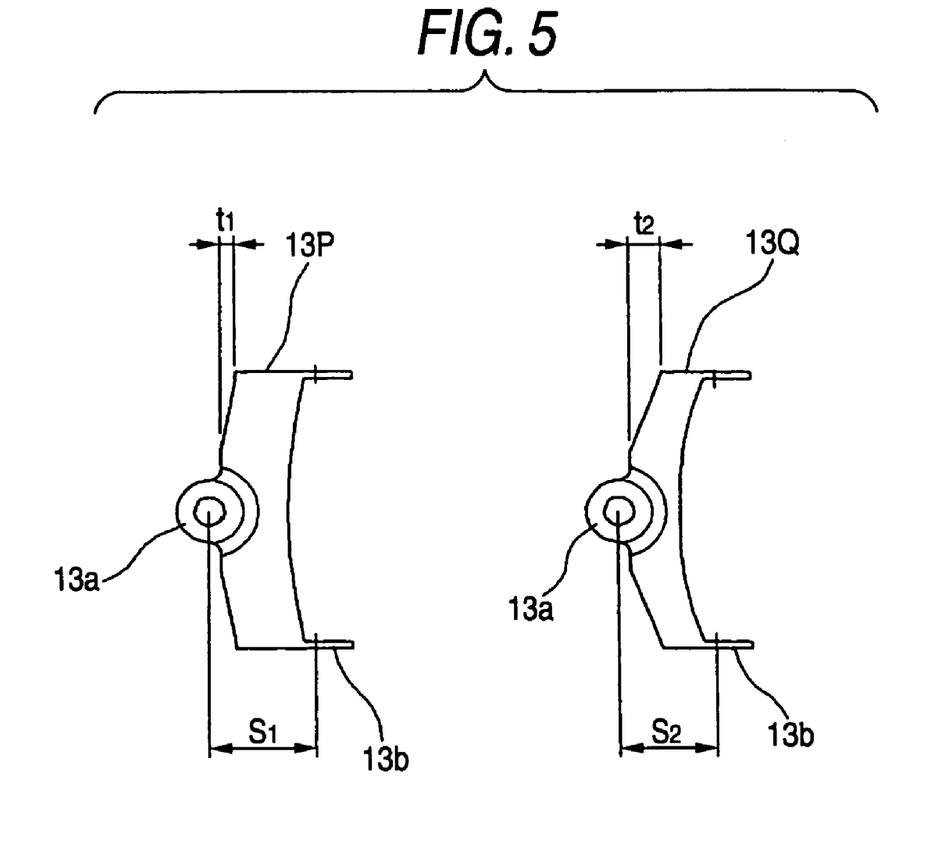
FIG. 5 is a front view of two types of angle rings used in angle ring units.

Firstly, two types of angle rings that differ in the length dimension and the notch width dimension are used. Each angle ring unit 13U is arranged from two angle rings, and as shown in FIG. 5, for one angle ring 13P of the two types of angle rings, the length dimension, specifically, the interval, from the center of the pin insertion hole of the pivoting joint portion 13a to the center of the pin insertion hole of the pivoting joint portion 13a, is indicated as $s_1$ and the width of the notched portion in the phase direction of 90° from the pivoting joint portion is indicated as $t_1$, and for the other angle ring 13Q, the length dimension is indicated as $s_2$ and the notch width is indicated as $t_2$. Here, the dimensional relationships $s_1 > s_2$ and $t_1 < t_2$ are made to hold.

Figure 6A:
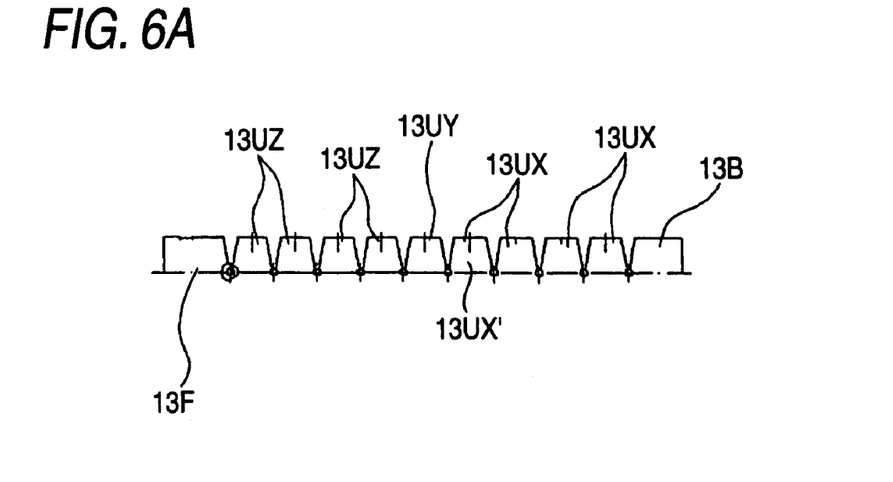
FIGS. 6A and 6B are arrangement explanation diagrams of a state in which an angle portion structure is extended straightly and a state in which the angle portion structure is bent by 90°.

The external appearance of the upper half of the angle portion structure 10 is shown in FIG. 6A. As is clear from this figure, in regard to the angle ring units, the structure is arranged from angle ring units 13UX, in each of which two angle rings 13P are connected, an angle ring unit 13UY, in which an angle ring 13P and an angle ring 13Q are connected, and angle ring units 13UZ, in each of which two angle rings 13Q are connected. The length dimension S of each angle ring unit 13UX is $2s_1$ and thus the largest, the length dimension S of the angle ring unit 13UY is $(s_1+s_2)$ and is thus of intermediate magnitude, and the length dimension S of each angle ring unit 13UZ is $2s_2$ and thus the smallest. From the base end connection ring 13B, a predetermined number of angle ring units 13UX (corresponding to third angle units) are connected successively, and from the front end connection ring 13F, a predetermined number of angle ring units 13UZ are connected successively. One angle ring unit 13UY is disposed in the middle. In this embodiment, the angle ring unit 13UY corresponds to an angle unit adjacent to the distal one 13UX' of the angle ring units 13UX (third angle units).

Due to the above, the total notch width is $2t_1$ and is the smallest at each connection portion at which the angle ring units 13UX are connected to each other and at the portion of connection of 13UX with 13UY, the total notch width is $t_1+t_2$ and thus of intermediate value at the portion of connection of the angle ring units 13UY and 13UZ, and the total notch width is $2t_2$ and is the largest at each of the portions of connection of the angle ring units 13UZ with each other.

Figure 6B:
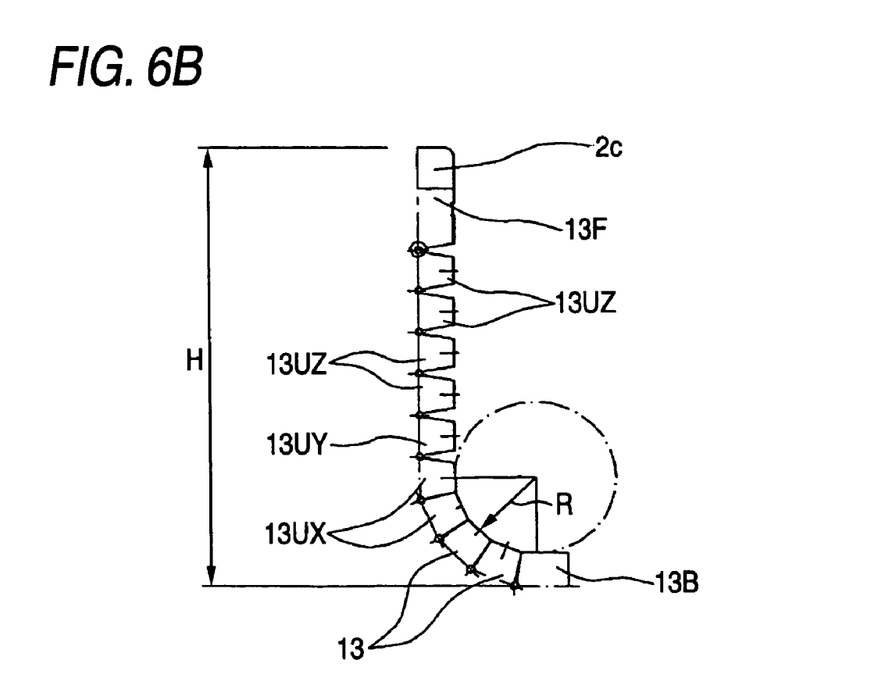

When the angle portion 2b is bent by applying tension to an operating wire 16, the angle portion 2b does not begin to bend as a whole but becomes bent successively from the base end side. That is, the wall surfaces that make up the notched portions between the base end connection ring 13B and the adjacent angle ring unit 13UX contact each other, then the wall surfaces making up the notched portions between this angle ring unit 13UX and the angle ring unit 13UX positioned in front contact each other, and bending is performed successively towards the front end side. Thus, in the middle of the bending operation of angle portion 2b, there exists a state wherein although the base end side is bent, the front end side is straight as shown in FIG. 6B. That is, when the angle portion 2b is operated to become bent, first its base end side is made upright and the front end side becomes bent and the state of maximum curvature is reached via the state of FIG. 6B.

In the state in which the angle portion 2b is bent at an angle of 90° as shown in FIG. 6B and thus in the state of maximum curvature, the radius of curvature of the angle ring units 13UX becomes R, and of the total length of the angle portion 2b, the portion, corresponding to arc angle positions making up ¼th of the circle of radius of curvature R, is arranged from the angle ring units 13UX. The radius of curvature at the portion of the starting end of bending can thus be made large. If the angle portion 2*b* is arranged from the angle ring units 13UX over its entire length, the height H will become extremely high. However, since a single angle ring unit 13UY, which is shorter in length than angle ring unit 13UX, and a plurality of angle ring units 13UY, which are even shorter, are disposed at the front end side of the angle ring units 13UX, the height dimension H when the angle portion 2*b* is made upright to an angle of 90° from the axial line of the insertion portion 2 can be made correspondingly lower. In the locus of movement of the distal end hard portion 2*c* in the process of a bending operation of the angle portion 2*b*, the widest space becomes necessary when the angle portion 2*b* is made upright to 90° with respect to the axial line of the insertion portion. Here by restraining this height H to the minimum, the locus of movement is made compact, the angle portion 2*b* is made good in operability, and pain inflicted on the subject can be lightened.

When the angle portion 2*b* is put in the maximally bent state, the portion made up of the angle ring units 13UZ, which are positioned along the extension of the portion made up of the angle ring units 13UX, becomes small in radius of curvature than the portion made up of the angle ring units 13UX. However, since the angle ring unit 13UY exists in between, the transition of the radius of curvature is relaxed, and since bending occurs at a stage prior to this transition portion, the transition of the radius of curvature corresponds to the difference in the radii of curvature of the angle ring units 13UX and the angle ring units 13UZ. The degree of change of bending will thus be small. Thus, when in the state in which the angle portion 2*b* is maximally bent, an operative instrument is inserted inside the operative instrument insertion channel 5, since the operative instrument will be put in a gradually bent state initially and will become bent further by just the difference in the radii of curvature at the portion of transition of the radius of curvature, smooth insertion operability is secured. On the other hand, if the angle ring units 13UZ are connected across the entire length of the angle portion 2*b*, the radius of curvature of the angle portion 2*b* as a whole will be small and the insertability of the operative instrument will be poor.

Even if the length dimensions of the angle ring units are varied in a continuous manner or the width dimensions of the notched portions are varied in a continuous manner, the height dimension H will become higher or the radius of curvature R will become smaller, or the height dimension H will become higher and the radius of curvature R will become smaller in comparison to the above-described arrangement of the present invention.

By appropriately setting the numbers and shapes of the angle ring units 13UX and the angle ring units 13UZ, the required angle of curvature can be realized.

By the above arrangement, the angle portion can be enabled to be bent compactly without placing restrictions on the angle of curvature of the angle portion, the curvature of bending can be made large to enable smooth angle operation inside a narrow body cavity, the pain inflicted on a subject can be lowered, and the operability of insertion of operative instruments can be improved.

The entire disclosure of each and every foreign patent application from which the benefit of foreign priority has been claimed in the present application is incorporated herein by reference, as if fully set forth.

What is claimed is:

1. An endoscope angle portion comprising
an angle portion structure including
angle ring units each of which comprises pivoting joint portions extending from its both ends and has a shape that is notched obliquely in directions away from the pivoting joint portions, and
wherein adjacent ones of the angle ring units is pivotally joined to form the angle portion structure,
wherein a first angle ring unit of the angle ring units has a larger length dimension than that of a second angle ring unit of the angle ring units, and the first angle ring unit has a smaller notch width of a notched portion than that of the second angle ring unit, the first angle ring unit being nearer a base end of the endoscope angle portion than the second angle ring unit,
wherein, third angle ring units of the angle ring units form an arc spanning approximately ¼th of a circle in a state in which the angle portion structure is bent to a maximum curvature of bending, the third angle ring units being nearest the base end of the endoscope angle portion and wherein an angle ring unit adjacent the distal one of the third angle ring units has a different length dimension from that of the distal one of the third angle ring units, and has a different notch width in a notched portion from that of the distal one of the third angle ring units.

2. The endoscope angle portion according to claim 1, wherein each of the angle ring units comprises a pair of angle rings so as to bend to left direction and right direction of the endoscope angle portion, and the angle ring units are provided in an axial line direction of the endoscope angle portion so that the angle portion structure can bend upward and downward direction.

* * * * *